United States Patent [19]

Henrick et al.

[11] 4,000,315
[45] Dec. 28, 1976

[54] CYCLOPROPANE ESTERS FOR THE CONTROL OF MITES

[75] Inventors: Clive A. Henrick; Gerardus B. Staal, both of Palo Alto, Calif.

[73] Assignee: Zoecon Corporation, Palo Alto, Calif.

[22] Filed: July 14, 1975

[21] Appl. No.: 595,654

Related U.S. Application Data

[62] Division of Ser. No. 504,224, Sept. 9, 1974, Pat. No. 3,957,849.

[52] U.S. Cl. .............................. 424/305; 424/307
[51] Int. Cl.$^2$ ........................................ A01N 9/24
[58] Field of Search ......................... 424/305, 307

[56] References Cited

FOREIGN PATENTS OR APPLICATIONS 2,042,295   3/1971   France ............................ 260/468

Primary Examiner—Jerome D. Goldberg
Assistant Examiner—Allen J. Robinson
Attorney, Agent, or Firm—Donald W. Erickson

[57] ABSTRACT

Esters of cyclopropyl substituted carboxylic acids, syntheses thereof, compositions thereof, and use for the control of mites and ticks.

12 Claims, No Drawings

CYCLOPROPANE ESTERS FOR THE CONTROL OF MITES

This is a division of application Ser. No. 504,224, filed Sept. 9, 1974, U.S. Pat. No. 3,957,849.

This invention relates to novel compounds, synthesis thereof, compositions thereof, and the control of mites.

The compounds of the present invention are effective for the control of mites and especially spider mites. Spider mites are plant feeders and cause serious damage to orchard trees, field crops, greenhouse plants and other vegetation. They feed on the foliage and fruit of plants and trees and attack a variety of plants and trees due to their wide distribution and polyphagous feeding habits. Spider mites of the family Tetranychidae, such as *Tetranychus urticae*, *Tetranychus canadensis*, *Tetranychus cinnabarinus*, *Tetranychus pacificus*, *Bryobia praetiosa*, *Oligonychus pratensis*, *Oligonychus ilicis*, *Panonychus citri*, *Panonychus ulmi*, and similar related species, are of particular biological interest and economic importance. Other mites are those of the family Tarsonemidae, such as *Steneotarsonemus pallidus*.

Compounds of the present invention of the following formula I are effective control agents for mites.

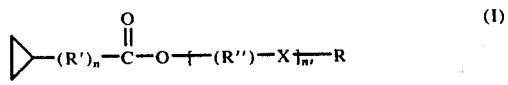
(I)

wherein,

R is alkyl of one to eighteen carbon atoms, alkenyl of two to eighteen carbon atoms, alkynyl of two to eighteen carbon atoms, cycloalkyl, aryl, or aralkyl, each of said cycloalkyl, aryl, or aralkyl rings being optionally substituted by one or two alkyl, alkoxy, halogen or nitro groups;

R' is —CH=CH— or —(CH$_2$)$_p$— in which $p$ is an even integer from two to 20;

R'' is ethylene or propylene;

X is oxygen or sulfur;

$n$ is zero or one; and $n'$ is one, two or three;

with the proviso that each compound contains at least twelve carbon atoms in the molecule.

Hereinafter, each of R, R', R'', X, $n$, $n'$ and $p$ is as defined above unless otherwise specified.

The compounds of formula I are applied to the mite during the egg, larval or nymphal stages in view of their effect in causing inhibition of egg hatching, abnormal development leading to death, inability to pass from one stage to the next, or inability to reproduce. Some of the compounds also exhibit a residual ovicidal effect on foliage. A compound of formula I can be applied at concentration levels of the order of 0.001% to 1%, usually 0.01 to 0.1% by weight. Suitable carrier substances include liquid or solid inert carriers, such as water, acetone, xylene, mineral or vegetable oils, talc, vermiculite, and silica. Treatment of mites in accordance with the present invention can be accomplished by spraying, dusting, or otherwise contacting the mites and/or their eggs or larvae directly or indirectly. Generally, a concentration of less than 25% of active compound in the formulation is used depending on the type of application apparatus. The formulations can include emulsifying agents and wetting agents to assist in the application and effectiveness of the active ingredient.

The esters of formula I can be prepared by reacting the appropriate mono-hydric alcohol R+X-R''+$_{n'}$ OH with one mole of an acid of the formula

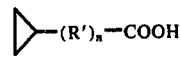

in the presence of an acid catalyst and with heating. The reaction can be carried out in the absence of a solvent; however, use of a solvent inert to the reaction, such as an ether or hydrocarbon solvent, is preferred. Water may be removed by azeotropic distillation, if desired.

Alternatively, the appropriate acid halide

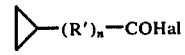

may be reacted with the corresponding mono-hydric alcohol in the presence of pyridine and at either room temperature or, when the alcohol is sensitive to mineral acid, at from about −10° to about 0° C.

Many of the monohydric alcohols used in the preparation of novel compounds of this invention are commercially available. Typical of these are the monomethyl ether of ethylene glycol and the monomethyl ether of propylene glycol.

Alcohols of the formula R+O—R''+$_{n'}$ OH where $n'$ is one can be prepared by reacting ethylene oxide or propylene oxide with an alcohol ROH in the presence of a sodium alkoxide at a temperature of from 35° to 70° C or by reacting ethylene chlorohydrin or propylene chlorohydrin with an alcohol ROH in the presence of sodium. For those alcohols where $n'$ is two, the above process is repeated with the alcohol R+ OR''+ OH from that process being reacted with the ethylene oxide or propylene oxide in the presence of a sodium alkoxide. The process is again repeated to yield those alcohols where $n'$ is three.

Alcohols of the formula R+ S—R''+$_{n'}$ OH can be prepared by reacting ethylene chlorohydrin or 2-chloropropanol with a thiol RSH in the presence of sodium at from 30° to 150° C. To prepare those alcohols where $n'$ is two or three, the compound R+S—R''+$_{n'}$ OH is treated with toluenesulfonyl chloride followed by NaSH and dimethyl formamide. The resultant thiols RS—(R'')n'—SH are then reacted with ethylene chlorohydrin or 2-chloropropanol as above to yield those alcohols where $n'$ is two. The entire sequence is again repeated to obtain those compounds where $n'$ is three.

The syntheses of the acids

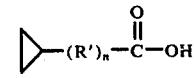

and acid chlorides are described in copending Ser. No. 461,189, filed Apr. 12, 1974, now U.S. Pat. No. 3,925,460, and copending Ser. No. 489,207, filed July 17, 1974, now U.S. Pat. No. 3,960,907, the disclosures of which are hereby incorporated by reference.

The term "alkyl," as used herein, refers to a straight or branched chain saturated aliphatic hydrocarbon group of 1 to 18 carbon atoms, e.g. methyl, ethyl, propyl, octyl, 2-methyloctyl, undecyl, pentadecyl, and the like. The term "lower alkyl" refers to an alkyl group of 1 to 6 carbon atoms.

The term "alkenyl," as used herein, refers to a straight or branched chain hydrocarbon group of 2 to 18 carbon atoms having one or two sites of olefinic unsaturation.

The term "alkynyl," as used herein, refers to a straight or branched chain hydrocarbon group of 2 to 18 carbon atoms having one or two sites of acetylenic unsaturation.

The term "cycloalkyl," as used herein, refers to a mono-valent cycloalkyl moiety of 4 to 18 carbon atoms, i.e. cyclobutyl, cyclopentyl, cyclohexyl, cycloheptyl, and cyclooctyl.

The term "aryl," as used herein, refers to a monovalent aromatic hydrocarbon group containing from 6 to 14 carbon atoms, such as phenyl, biphenyl, and naphthyl.

The term "aralkyl," as used herein, refers to a monovalent hydrocarbon group containing from 7 to 15 carbon atoms in which a hydrogen atom of an alkyl group having a chain length of 1 to 6 carbon atoms is substituted by an aryl group, such as benzyl, phenethyl, methylbenzyl, naphthylmethyl and naphthylethyl.

The term "alkoxy," as used herein, refers to a straight or branched chain saturated aliphatic hydrocarbonoxy group of 1 to 15 carbon atoms, e.g., methoxy, ethoxy, n-propoxy, i-propoxy, n-butoxy, n-heptyloxy, n-dodecyloxy, 2-methyloctyloxy, and the like.

The term "halogen," as used herein, refers to fluorine, chlorine, and bromine.

The esters of the present invention can be used alone or in inert carrier substance for the control of mites (Acarina) or can be used in mixture with pesticides and/or juvenile hormone analogs known in the art in order to obtain a broader spectrum of activity. Suitable insecticides include Baygon, Captan, Sevin, Ciodrin, Systox, Diazinon, Vapona, Galecron, Cygon, Dimethrin, Dursban, Malathion, and Parathion. Typical juvenile hormone analogs which can be used in mixture with the compound of the present invention are described in U.S. Pat. Nos. 3,752,843 and 3,755,411.

The esters of the present invention are useful for the control of mites and ticks which are ectoparasitic on domestic animals including birds. The compounds can be applied in either solution or in powder (dust) form in a conventional manner.

The following examples are provided to illustrate the synthesis of the esters of the present invention and the practice of the present invention. Temperature is in degrees Centigrade. All boiling points were measured by short path distillation.

EXAMPLE 1

To 14.0 ml. of anhydrous 1-pentanol in 100 ml. tetrahydrofuran is added 0.25 g. sodium. After the sodium has reacted, gaseous ethylene oxide (0.34 g.) is added at a rate such that the temperature is maintained between 35° and 40°. The flask is sealed and allowed to stand for one day. The reaction mixture is poured into water and then extracted with ether, dried over sodium sulfate, the solvent and the residue distilled and fractionated to yield 2-pentyloxy-1-ethanol.

Using the procedure of Example 1, each of ethylene oxide and propylene oxide is reacted with each of 1-dodecanol, 1-tridecanol, 1-tetradecanol, 1-pentadecanol, cyclohexanol, phenol, benzyl alcohol, 4-methoxyphenol, 4-methylphenol, 2-decyn-1-ol, tetradeca-10,12-dien-1-ol, hexadec-9en-1-ol, octadec-9-yn-1-ol and 7-methyltrideca-5,8-diyn-7-ol to yield the alcohols of column I.

I 2-(dodecyloxy)ethanol
2-(dodecyloxy)-1-methylethan-1-ol
2-(tridecyloxy)ethanol
1-methyl-2-tridecyloxyethan-1-ol
2-(tetradecyloxy)ethanol
1-methyl-2-(tetradecyloxy)ethan-1-ol
2-(pentadecyloxy)ethanol
1-methyl-2-(pentadecyloxy)ethan-1-ol
2-(cyclohexyloxy)ethanol
2-(cyclohexyloxy)-1-methylethan-1-ol
2-(phenoxy)ethanol
1-methyl-2-(phenoxy)ethan-1-ol
2-(benzyloxy)ethanol
2-(benzyloxy)-1-methylethan-1-ol
2-(4-methoxyphenoxy)-1-ethanol
2-(4-methoxyphenoxy)-1-methyl-1-ethanol
2-(4-methylphenyl)ethan-1-ol
2-(4-methylphenoxy)-1-methylethan-1-ol
2-decynyloxyethanol
2-decynyloxy-1-methylethan-1-ol
tetradeca-10,12-dienloxyethanol
1-methyl-2-tetradeca-10,12-dienyloxyethan-1-ol
2-hexadec-9-enyloxyethan-1-ol
2-hexadec-9-enyloxy-1-methylethan-1-ol
2-octadec-9-ynyloxyethan-1-ol
1-methyl-2-octadec-9-ynyloxyethan-1-ol
2-(7-methyltrideca-5,8-diyn-7-yloxy)ethan-1-ol
1-methyl-2-(7-methyltrideca-5,8-diyn-yloxy)ethan-1-ol

EXAMPLE 2

To a mixture of 0.25 g. sodium hydride in 25 ml. anhydrous tetrahydrofuran is added 0.5 g. methanethiol. The reaction mixture is stirred for 2 hours and the solvent is then removed by evaporation. To the residue is added, at 35°, 5 ml. water and 6 g. of 20% aqueous ethylene chlorohydrin. The reaction mixture is stirred for 30 minutes and then refluxed for 1 hour. After cooling to room temperature, ether is added, the organic phase is separated and washed in turn with 10% aqueous sodium bicarbonate, water, 2N sulfuric acid, water, and brine. The solution is dried over calcium carbonate and the solvent is removed by evaporation to yield 2-methylthio-1-ethanol.

Following the procedure of Example 2, each of ethylene chlorohydrin and 1-chloro-2-propanol is reacted with each of 1-dodecanethiol, 1-tetradecanethiol, 1-butanethiol, benzenethiol, cyclohexanethiol, 1-propanethiol and 2-methylthio-1-ethanethiol to yield the alcohols of column II.

II 2-(dodecylthio)ethanol
1-methyl-2-(dodecylthio)ethanol
2-(tetradecylthio)ethanol
1-methyl-2-(tetradecylthio)ethan-1-ol
2-(butylthio)ethanol
2-(butylthio)-1-methylethan-1-ol
2-(phenylthio)ethanol
1-methyl-2-(phenylthio)ethan-1-ol
2-(cyclohexylthio)ethanol
2-(cyclohexylthio)-1-methylethan-1-ol 2-(propylthio)ethanol
1-methyl-2-(propylthio)ethan-1-ol
3,6-dithiaheptanol
3,6-dithia-1-methylheptanol-2-ol

EXAMPLE 3

A. To a mixture of 9.6 g. 1-tridecanol and 100 ml. tetrahydrofuran at 0° is added 33.5 ml. of 1.43 M n-butyllithium in hexane over a 5 minute period. The reaction mixture is allowed to warm to room temperature and is stirred for 1 hour. The solvent is removed by evaporation and to the colorless viscous residue is added 100 ml. tetrahydrofuran and 50 ml. hexamethylphosphoric triamide followed by 20 g. sodium iodoacetate. The mixture is stirred at room temperature overnight and then boiled for 8.5 hours. After cooling to room temperature, 150 ml. methanol, 75 ml. water, and 3.8 g. sodium hydroxide pellets are added. The mixture is boiled for 12 hours, cooled to room temperature, and allowed to stand 15 days. The solvent is removed by evaporation and to the residue is added 400 ml. of a 2:1 mixture of ether and pentane and 200 ml. water. The top two phases of the resultant triphasic mixture are separated and washed twice with 100 ml. portions of water. Ethyl acetate, water and sulfuric acid are added; after vigorous shaking the mixture is filtered and the filtrate is washed two times with 50 ml. portions of sodium chloride and then dried over calcium sulfate.

B. To a mixture of 2.58 g. 3-oxahexadecanoic acid and 15 ml. anhydrous tetrahydrofuran at 0° is added 12 ml. of a 1M diborane in tetrahydrofuran solution. The ice-bath is removed after the bubbling stops and the mixture is stirred overnight. Slowly, 20 ml. water is added and the solution is stirred 15 minutes after the initial bubbling ceases. Ester (100 ml.), water (100 ml.) and aqueous 3N sulfuric acid (30 ml.) are added and the organic phase is separated and washed in turn with 40 ml. water and 40 ml. aqueous saturated sodium chloride and then dried over calcium sulfate. Solvent is removed by evaporation to yield 1.75 g. 3-oxahexadecanol, to which is added 60 ml. anhydrous ether. The solution is cooled to 0° and 1.12 g. cyclopropane carboxylic acid chloride and 1.2 ml. pyridine is added. The reaction mixture is allowed to warm to room temperature and is stirred for 4 days. The mixture is then filtered, 1 ml. water is added and the solution is stirred for 18 hours. Ether (50 ml.), pentane (50 ml.), and water (100 ml.) are added and the mixture is acidified with aqueous 3N sulfuric acid. The organic layer is separated and washed, in turn, with aqueous 15% potassium carbonate (1 × 50 ml.), water (2 × 50 ml.), aqueous saturated copper sulfate (1 × 50 ml.), water (1 × 50 ml.), aqueous saturated sodium chloride (1 × 50 ml.) and dried over calcium sulfate. The solvent is removed by evaporation to yield 1.70 g. 3-oxahexadecyl cyclopropanecarboxylate.

Following the procedure of Example 3, 3-oxahexadecanol is reacted with each of 3-cyclopropylpropionyl chloride and 3-cyclopropyl-2-propenoyl chloride to yield the esters of column III.

III 3-oxahexadecyl 3-cyclopropylpropionate
3-oxahexadecyl 3-cyclopropyl-2-propenoate

EXAMPLE 4

To a mixture of 2.0 g. cyclopropanecarboxylic acid chloride, 60 ml. anhydrous ether, and 2.56 g. 3,6,9-trioxaundecanol, at 0°, is added 2.3 ml. pyridine. The reaction mixture is stirred at room temperature and then is filtered, 1 ml. water is added to the filtrate and the mixture is stirred overnight. Ether (50 mi.), pentane (50 ml.), and water (100 ml.) are added and the mixture is acidified with 3N sulfuric acid. The mixture is worked up using the procedure of Example 3 to yield 1.30 g. of 3,6,9-trioxaundecyl cyclopropanecarboxylate, b.p. 86°–94° (0.03 mm).

Following the procedure of Example 4, each of cyclopropanecarboxylic acid chloride and 3-cyclopropylpropionyl chloride is reacted with each of the alcohols of column IV to yield the esters of this invention, representative members of which are listed in column V.

IV 3,6,9-trioxatridecanol
2-(dodecyloxy)ethanol
2-(dodecyloxy)methyl-1-ethanol
2-(tridecyloxy)ethanol
1-methyl-2-tridecyloxyethanol
2-(tetradecyloxy)ethanol
1-methyl-2-(tetradecyloxy)ethanol
2-(pentadecyloxy)ethanol
1-methyl-2-(pentadecyloxy)ethanol
2-(cyclohexyloxy)ethanol
2-(cyclohexyloxy)-1-methylethanol
2-(phenoxy)ethanol
1-methyl-2-(phenoxy)ethanol
2-(benzyloxy)ethanol
2-(benzyloxy)-1-methylethanol
2-(4-methoxyphenyl)ethanol
1-methyl-2-(4-methoxyphenyl)ethanol
2-(4-methylphenyl)ethanol
1-methyl-2-(4-methylphenyl)ethanol

V 3,6,9-trioxatridecyl cyclopropanecarboxylate
2-(dodecyloxy)ethyl cyclopropanecarboxylate
2-dodecyloxy-1-methylethyl cyclopropanecarboxylate
1-methyl-2-(tridecyloxy)ethyl cyclopropanecarboxylate
2-(tetradecyloxy)ethyl-3-cyclopropylpropionate
1-methyl-2-(tetradecyloxy)ethyl 3-cyclopropylpropionate
2-(pentadecyloxy)ethyl cyclopropanecarboxylate
1-methyl-2-(pentadecyloxy)ethyl 3-cyclopropylpropionate
2-(cyclohexyloxy)ethyl cyclopropanecarboxylate
2-(cyclohexyloxy)-1-methylethyl 3-cyclopropylpropionate
2-(phenoxy)ethyl 3-cyclopropylpropionate
1-methyl-2-(phenoxy)ethyl cyclopropanecarboxylate
2-(benzyloxy)ethyl cyclopropanecarboxylate
2-benzyloxy-1-methylethyl 3-cyclopropylpropionate
2-(4-methoxyphenyl)ethyl 3-cyclopropylpropionate
2-(4-methoxyphenyl)-1-methylethyl 3-cyclopropylpropionate
2-(4-methylphenyl)ethyl cyclopropanecarboxylate
2-(4-methylphenyl)-1-methylethyl cyclopropanecarboxylate

EXAMPLE 5

To a mixture of 2.0 g. 2-hydroxyethyl dodecyl sulfide, 60 ml. anhydrous ether and 1.27 g. cyclopropyl carboxylic acid chloride at 0° is added 1.3 ml. pyridine.

The mixture is allowed to warm to room temperature and is stirred for three days. The product is isolated using the procedure of Example 3 to yield 3-thiapentadecyl cyclopropanecarboxylate, boiling point 131°—137° (0.03 mm.).

Following the procedure of Example 5, the compounds of column II are reacted with each of cyclopropanecarboxylic acid chloride, 3-cyclopropylpropionyl chloride, 5-cyclopropylpentanoyl chloride, 7-cyclopropylheptanoyl chloride and 9-cyclopropylnonanoyl chloride to yield the esters of this invention, representative examples of which are listed in column VI.

VI 2-(tetradecylthio)ethyl cyclopropanecarboxylate
1-methyl-2-(tetradecylthio)ethyl 3-cyclopropylpropionate
2-(butylthio)ethyl 5-cyclopropylpentanoate
2-(butylthio)-1-methylethyl 7-cyclopropylheptanoate
2-(phenylthio)ethyl 3-cyclopropylpropionate
1-methyl-2-(phenylthio)ethyl cyclopropanecarboxylate
2-(cyclohexylthio)ethyl 3-cyclopropylpropionate
2-(cyclohexylthio)-1-methylethyl 5-cyclopropylpentanoate
2-(propylthio)ethyl 7-cyclopropylheptanoate
1-methyl-2-(propylthio)ethyl 9-cyclopropylnonanoate
3,6-dithiaheptyl 7-cyclopropylheptanoate
4,7-dithiaoctyl 5-cyclopropylpentanoate

EXAMPLE 6

To a mixture of 3.5 g. 2-(4-biphenyloxy)ethanol, 80 ml. anhydrous tetrahydrofuran, and 2.56 g. cyclopropanecarboxylic acid chloride, at 0°, is added 2.6 ml. pyridine. The reaction mixture is allowed to warm to room temperature and then is stirred for 9 days. The mixture is filtered and to the filtrate is added 0.5 ml. water followed by stirring for 6 hours at room temperature. Solvent is removed by evaporation and to the residue is added 100 ml. ether, 60 ml. ethyl acetate, and 150 ml. water. The organic layer is separated, acidified with 3N sulfuric acid and washed in turn with aqueous 10% potassium carbonate, water, saturated aqueous copper sulfate, water, and saturated aqueous sodium chloride, dried over calcium sulfate and the solvent removed to yield 2.13 g. biphenyloxyethyl cyclopropanecarboxylate as pale yellow crystals.

Following the procedure of Example 6, 2-naphthyloxyethyl cyclopropanecarboxylate and 2-(2-phenoxyethoxy)ethyl cyclopropanecarboxylate are prepared from cyclopropanecarboxylic acid chloride and each of 2-(naphthyloxy)ethanol and 2-(2-phenoxyethoxy)ethanol.

EXAMPLE 7

To a mixture of 1.88 g. 2-(4-chlorophenylthio)ethanol and 1.35 g. cyclopropylcarboxylic acid chloride in 50 ml. ether is added 2 equivalents pyridine. The reaction mixture is stirred overnight at room temperature and worked up as in Example 5 to yield 2-(4-chlorophenylthio)ethyl cyclopropanecarboxylate.

A wettable powder suitable for field application after dilution can be formulated by blending and then air-mailing a mixture of 20 to 30% of an ester of this invention, 60 to 70% of a solid carrier such as Attaclay X-250, 1 to 3% of an anionic surfactant, such as Igepon T-77, and 3 to 5% of a dispersing agent such as Marasperse N-22.

A typical formulation is as follows:

| | |
|---|---|
| Active ingredient[1] | 25.0% |
| Synthetic calcium silicate | 40.0% |
| Attapulgite Clay | 29.0% |
| Sodium lignosulfonate | 4.0% |
| Sodium N-methyl N-oleoyl taurate | 2.0% |

[1]The active ingredient is selected from one or more of the following:
3-thiapentadecyl cyclopropanecarboxylate
3-thiapentadecyl 3-cyclopropylpropionate
3-oxahexadecyl cyclopropanecarboxylate
2-(4-chlorophenylthio)ethyl cyclopropanecarboxylate The mite control agents of the present invention can be used alone in an inert agriculturally acceptable carrier substance for the control of mites (Acarina) or can be used in mixture with insecticides and/or juvenile hormone analogs known in the art to provide a broader spectrum of activity on more developmental stages of the mites or on other pestiferous insect species.

The effectiveness of the compunds of the present invention is demonstrated below.

Adults of Tetranychus urticae are allowed to oviposit for 24 hours on castor bean leaf discs (diameter 1 cm.) on moist cottonwool.

After 24 hours, the adults are removed and the leaf discs are then dipped in acetone solutions of the compound being tested.

After submersion for one second, the solvent on the leaf discs is allowed to dry and the leaf discs are then glued to a plastic petri dish to prevent crumpling.

Six days later (when all the viable eggs on untreated discs have emerged), the number of unhatched eggs is calculated as a percentage of the total number originally present and corrected for any spontaneous non-emergence observed in control discs treated only with solvent (Abbott correction).

Table 1 presents the results of biological testing conducted as outlined above.

TABLE I

| Compound | % Concentration in solution | Reduction of Hatching in % |
|---|---|---|
| 3-oxahexadecyl cyclopropanecarboxylate | 0.1 | 95 |
| 2-(4-chlorophenylthio)ethyl cyclopropanecarboxylate | 0.1 | 97 |
| 3-thiapentadecyl cyclopropanecarboxylate | 0.1 | 100 |

We claim:

1. A method for the control of mites of the family Tetranychidae and the family Tarsonemidae which comprises contacting the mite at the egg or larval stage with an ovicidally effective amount or larvacidally effective amount of a compound of formula (I):

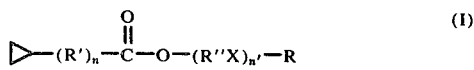

wherein,
R is alkyl of one to eighteen carbon atoms, alkenyl of two to eighteen carbon atoms, alkynyl of two to eighteen carbon atoms, cyclohexyl, phenyl, biphenyl or benzyl, each of said cyclohexyl, phenyl, biphenyl or benzyl being optionally substituted by one or two groups selected from the group consisting of methyl, ethyl, methoxy, ethoxy, chloro and nitro;

R' is —CH=CH— or —(CH$_2$)$_p$- in which $p$ is an even integer for two to twenty;

R'' is ethylene or propylene;

X is oxygen or sulfur;

$n$ is zero or one; and $n'$ is 1, 2 or 3, with the proviso that each compound contains at least 12 carbon atoms.

2. The method according to claim 1 wherein the compound is 3-oxahexadecyl cyclopropanecarboxylate.

3. The method according to claim 1 wherein the compound is 2-(4-chlorophenylthio)ethyl cyclopropanecarboxylate.

4. The method according to claim 9 wherein the compound is a compound of the formula:

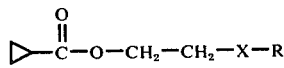

wherein X is oxygen or sulfur and R is dodecyl or tridecyl.

5. The method according to claim 4 wherein the compound is 3-thiapentadecyl cyclopropanecarboxylate.

6. The method according to claim 4 wherein the compound is 3-oxapentadecyl cyclopropanecarboxylate.

7. A composition for the control of mites of the family Tetranychidae or the family Tarsonemidae which comprises a suitable carrier substance and a compund of formula (I):

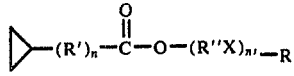 (I)

wherein,

R is alkyl of 1 to 18 carbon atoms, alkenyl of 2 to 18 carbon atoms, alkynyl of 2 to 18 carbon atoms, cyclohexyl, phenyl, biphenyl or benzyl, each of said cyclohexyl, phenyl, biphenyl or benzyl being optionally substituted by one or two groups selected from the group consisting of methyl, ethyl, methoxy, ethoxy, chloro and nitro;

R' is —CH=CH— or (CH$_2$)$_p$— in which $p$ is an even integer from 2 to 20;

R'' is ethylene or propylene;

X is oxygen or sulfur;

$n$ is 0 or 1; and $n'$ is 1, 2 or 3, with the proviso that each compound contains at least 12 carbon atoms, said compound being present in the composition in an ovicidally effective amount or larvicidally effective amount.

8. The composition according to claim 7 wherein the compound is a compound of the formula

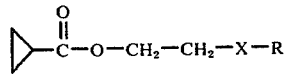

wherein X is oxygen or sulfur and R is dodecyl or tridecyl.

9. The composition according to claim 7 wherein the compound is 3-oxahexadecyl cyclopropanecarboxylate.

10. The composition according to claim 7 wherein the compound is 3-thiapentadecyl cyclopropanecarboxylate.

11. The composition according to claim 7 wherein the compound is 3-oxapentadecyl cyclopropanecarboxylate.

12. The composition according to claim 7 wherein the compound is 2-(4-chlorophenylthio)ethyl cyclopropanecarboxylate.

* * * * *

UNITED STATES PATENT OFFICE
CERTIFICATE OF CORRECTION

Patent No. 4,000,315           Dated December 28, 1976

Inventor(s)    Clive A. Henrick; Gerardus B. Staal

It is certified that error appears in the above-identified patent and that said Letters Patent are hereby corrected as shown below:

Col. 9, line 6, "for two" should read --from two--.

Claim 4, lin3 1, "claim 9" should read --claim 1--.

Signed and Sealed this

Third Day of May 1977

[SEAL]

*Attest:*

RUTH C. MASON
*Attesting Officer*

C. MARSHALL DANN
*Commissioner of Patents and Trademarks*